(12) United States Patent
Grune et al.

(10) Patent No.: US 8,129,133 B2
(45) Date of Patent: *Mar. 6, 2012

(54) DEVICES AND METHODS FOR THE RAPID, RELIABLE DETECTION AND DETERMINATION OF ACRYLAMIDE CONCENTRATION IN FOOD SUBSTANCES AND PREVENTION OF ACRYLAMIDE FORMATION IN THE SAME

(76) Inventors: Guerry L. Grune, Virginia Beach, VA (US); Todd Talarico, Cary, NC (US)

( * ) Notice: Subject to any disclaimer, the term of this patent is extended or adjusted under 35 U.S.C. 154(b) by 504 days.

This patent is subject to a terminal disclaimer.

(21) Appl. No.: 12/154,834

(22) Filed: May 27, 2008

(65) Prior Publication Data

US 2008/0268111 A1  Oct. 30, 2008

Related U.S. Application Data

(63) Continuation of application No. 10/710,801, filed on Aug. 4, 2004, now Pat. No. 7,393,903.

(51) Int. Cl.
*G01N 33/00* (2006.01)
*C07C 253/00* (2006.01)
*G03C 1/76* (2006.01)

(52) U.S. Cl. ........... 435/18; 558/333; 430/535; 436/106

(58) Field of Classification Search ........................ None
See application file for complete search history.

(56) References Cited

U.S. PATENT DOCUMENTS 5,854,010 A * 12/1998 Denison et al. ................... 435/8

OTHER PUBLICATIONS

Nawaz et al. Purification and Characterization of an Amidase From an Acrylamide-Degrading Rhodoccus SP.; Applied and Environmental Microbiology, vol. 60, No. 9 (1994) pp. 3343-3348.*

* cited by examiner

*Primary Examiner* — Rebecca Prouty
*Assistant Examiner* — Paul Martin
(74) *Attorney, Agent, or Firm* — Guerry L. Grune; ePatentmanager.com

(57) ABSTRACT

A device and associated analytical method to use for the sensitive detection and accurate, rapid determination of acrylamide in food substances is presented. Also described is the use of a kit device and associated analytical method in which a user can quickly and easily ascertain the amount of acrylamide in food substances with ease and in any location, including a non-laboratory environment. Such detection device and method may be comprised of a sample collection area on which a sample of food, after being mixed in a solution, is placed for example on the substrate of a biochip that includes an enzyme that along with a co-enzyme or catalyst, facilitates the conversion of either acrylamide to acrylonitrile or the conversion of acrylamide to ammonia.

2 Claims, 1 Drawing Sheet

DEVICES AND METHODS FOR THE RAPID, RELIABLE DETECTION AND DETERMINATION OF ACRYLAMIDE CONCENTRATION IN FOOD SUBSTANCES AND PREVENTION OF ACRYLAMIDE FORMATION IN THE SAME

This application is a continuation of and claims the benefit under 35 U.S.C. 120 of commonly assigned U.S. patent application Ser. No. 10/710,801 filed on Aug. 4, 2004, now U.S. Pat. No. 7,393,903 and entitled "DEVICES AND METHODS FOR THE RAPID, RELIABLE DETECTION AND DETERMINATION OF ACRYLAMIDE CONCENTRATION IN FOOD SUBSTANCES AND PREVENTION OF ACRYLAMIDE FORMATION IN THE SAME", filed Aug. 4, 2004, the entire disclosure of which is herein incorporated by reference for all purposes.

FIELD OF THE INVENTION

The field of the present invention relates to a device and associated analytical method that can be used for the sensitive detection and accurate, rapid determination of acrylamide in food substances. More specifically, the present invention also relates to the use of a kit device and associated analytical method in which a user can quickly and easily ascertain the amount of acrylamide in food substances and in any location, including a non-laboratory environment. Additionally, the invention also relates to the use of lower temperatures, removal of glucose or other related reducing sugars and/or potential food additives that would block or prevent the formation of acrylamides during food processing including baking, frying, etc.

Such a detection device and method may be comprised of a sample collection area on which a sample of food, after being mixed in a solution, is placed for example on the substrate of a biochip that includes an enzyme, such as nitrilase, that, along with a co-enzyme or form of energy or catalyst, facilitates the conversion of either acrylamide to acrylonitrile or the conversion of acrylamide to ammonia or other easily detectable chemical fragment of the acrylamide. A kit-like device could utilize an ammonia-sensitive or acrylonitrile-sensitive film strip, a display showing the amount of ammonia or acrylonitrile detected in the sample, preferably a calorimetric display utilizing a chromophore such as bromophenol blue, bromocresol green, or chlorophenol red which shows detection by color change, and a colorimetric scale to provide the kit user with the concentration of acrylonitrile or ammonia present, which can be scaled to be representative of the quantity of acrylamide in the food substance. If acrylamide is detected in the sample food substance, the resultant concentration, as determined on the colorimetric scale, provides the consumer of the food substance an opportunity to reject or discard the substance prior to digestion, thus promoting good health and avoiding potential ingestion of relatively high concentrations of the recently discovered carcinogenic potency of acrylamides.

Another variation of the detection device above may to utilize a mechanical or electrical pH balance meter and system similar to the calorimetric system utilized above, but which allows a numeric or digital reading of the concentration of acrylamides present in the sample of food. The use of digital pH balances is well known in the art and is an embodiment in the present invention to determine acrylamide concentrations accurately and precisely.

Another variation of the detection device above may utilize infrared (IR) spectrometry to measure a liquid sample and determine the amount of acrylonitrile or ammonia within the sample. For example, with acrylonitrile, the detection device may utilize an IR chemical sensor that identifies the very sharp absorption peak of the carbon-nitrogen C≡N triple bond in acrylonitrile. Because the C≡N triple bond is absorbed strongly in the IR spectra at 2250 cm$^{-1}$ wavelength, a hand-held or laboratory-based infrared sensor can be used to measure the IR adsorption. This provides a method to measure acrylonitrile precisely and accurately. The IR measurement component may be part of the test kit device or alternatively may be part of a test kit that is sent in to a laboratory for further analysis at that laboratory site.

Another variation of the detection device above may utilize a LUMI-CELL™ Assay that applies the knowledge of the toxic mechanisms of polychlorinated diaromatic hydrocarbons (PCDH). PCDH include dioxins and other toxic compounds that have been known to accumulate in animals and cause species and tissue-specific toxic effects. Birth defects, immune system disorders, tumor production, etc., have all been observed as a result of high level exposure to PCDH. It is anticipated that digestion of foods that contain high levels of acrylamides will cause similar toxic effects.

The U.S. Environmental Protection Agency defines acrylamide as an organic solid of white, odorless, flake-like crystals. It is primarily used in the treatment of drinking water and to produce plastics. Asparagine, a nonessential amino acid, and a known precursor to the formation of acrylamide in food, is present in starchy or fried foods—essentially most foods that contain carbohydrates and some that are primarily proteins, i.e. coffee beans. When asparagine is heated by high-temperature frying or baking (at a temperature that exceeds 120 degrees Celsius or 248 degrees Fahrenheit), and a sugar is present such as glucose or 2-deoxyglucose during the heating, the potential carcinogen acrylamide, as a monomer in foods, is formed. Conversely, acrylamide has not been detected in the same foods when left unheated, or heated at a temperature less than 120 degrees Celsius.

British and Swiss teams have both confirmed the original Swedish findings of acrylamide formation in food by invoking the Maillard reaction, or non-enzymatic browning. This reaction involves reactions between proteins and carbohydrates in food that cause browning when cooking. For example, this reaction is what gives freshly-baked bread its golden-brown crust. Thus, products of the Maillard reaction are used for the addition of both flavor and taste The mechanism of action for these compounds depends on their ability to bind to an intracellular receptor known as the aromatic hydrocarbon Receptor (AhR). The PCDH-Ah Receptor complex travels to the nucleus of the cell and binds to specific sequences in DNA known as dioxin responsive elements (DRE). Binding of the PCDH-Ah receptor complex to a DRE causes expression of the associated gene to be altered. It is this alteration in gene expression that causes observed toxic effects. Using recombinant technology, the gene for the firefly luciferase has been replaced under control of the Ah Receptor and inserted into a mouse cell line. Using this cell line, the presence of PCDH in a sample can be identified because PCDH will bind to the Ah Receptor, which will then bind to the DRE in the nucleus and cause expression of the firefly luciferase or green fluorescence protein or red fluorescence protein using a fluorometer to indicate activity which is proportional to concentration. The amount of PCDH in the sample is related to how much light is produced by the activated cells. It is anticipated that a similar mechanism will occur with acrylamides being substituted for PCDH and that binding to specific DNA sequences similar to DRE's will occur therefore allowing the use of the same technique and technology to measure acrylamide concentrations to less than the parts per trillion level. This technique has pioneered and championed by Drs. George C. Clark and Michael S. Denison and is fully described in U.S. Pat. No. 5,854,010 herein incorporated by reference.

Another possibility that exists in preparing a test method that could be used outside of the laboratory (as well as within a laboratory—as is the case for the other methods listed above), is that a reactive species within the acrylamide is made available to react with an amino acid in a protein. If this occurs within an animal (such as a mouse) that carries the protein, the body that carries the protein will "see" these reactive products as "foreign proteins" and production of monoclonal antibodies will occur. This decouples the test methodology from the cellular level as described in previous methods above. It is possible to then couple the antibodies with a color dye to indicate the concentration of antibodies that bind to the protein, while rinsing away those that do not bind. This method would also produce a highly sensitive test method and one that could be combined with a biochip for other than laboratory use (home or office use).

When heated, the asparagine, reducing sugars, and other amino acids react via the Maillard reaction, forming acrylamide. However, when asparagine alone is heated, no acrylamide is formed. Asparagine must be heated with a reducing sugar present. Proctor and Gamble in the US and the Canadian government have both confirmed this method of asparagine/acrylamide analysis and confirmed acrylamide formation via the Maillard reaction. FIG. 1 shows the chemical structures and reactions necessary for the formation of acrylamide from asparagine via the Maillard reaction.

Others involved in this area of science have also indicated that acrylamide may be formed from another plausible reaction pathway. It is indicated that acrylamide is formed by the loss of carbon dioxide through a natural metabolic process which is known as enzymatic decarboxylation. In this reaction the asparagine is the actual source of the acrylamide. Although this reaction would not occur under normal biological conditions, the reaction can occur at temperatures such as those above 100 degrees Celsius where fried foods are cooked.

It is another object of this invention to provide a means by which the Maillard reaction or the other pathways that lead to the formation of acrylamide can be completely blocked or prevented such as by removing reducing sugars, adding specific food additives, or simply changing the processing conditions for various carbohydrate containing foods that include asparagine as an amino acid or protein. Examples would include simply lowering process temperatures to below 120 degrees Celsius, adding acidic or basic components that would shift or alter the equilibrium reaction allowing for acrylamide formation, or removal of essential reducing sugars such as glucose by using sugar substitutes found to inhibit acrylamide formation.

In all cases, it may not be possible to completely eliminate acrylamide formation; however it is possible to reduce the absolute concentration in each food that is processed where acrylamide formation would otherwise occur in an unchecked manner, as is the current condition within the food processing industry.

Recent studies conclude that acrylamide has been found to cause cancer in laboratory animals. Such studies indicate the need for a quick, reliable, non-laboratory test kit that can be used to easily detect and measure acrylamide concentrations in food substances. These situations, in which acrylamides are present in food substances, should be easily detectable in order to provide ample opportunity to the test kit user to reject or discard the food substance in order to preserve personal health.

There are several known situations in which acrylamide formation is present in food. Acrylamide has been detected in foods cooked at high temperatures, such as those deep-fried or baked. Specific food substances, for example, that have been identified as containing acrylamide concentrations are: "French" fries from potatoes, potato chips, coffee, cereal products, and baked starchy foods such as bread. A device kit and analytical method for acrylamide testing will provide the user with a determination of acrylamide content found within such samples of food when measured.

There are currently at least two laboratory-based methods for detecting and quantifying acrylamide content in food substances: 1) liquid chromatography tandem (or two-stage) mass spectrometry (LC-MS/MS), and 2) gas chromatography-mass spectrometry (GC-MS). Either of these two tests requires an extensive lab environment and lab professional to conduct the test. These tests are both time intensive and expensive and the need exists to replace these tests with a quick and reliable alternative. Neither of these methods, although proven by several international studies to be reliable and to work sufficiently, would be easy or practical for an individual to use in a home or non-laboratory environment. This present invention, however, provides a device and method that is quick, reliable, practical and easy to use. Additionally, this invention does not require a laboratory to conduct the acrylamide detection and determination test; however a biochip could be also be used and sent to a laboratory for testing if no other alternative is available. The kit device is designed for home use or non-laboratory use so that a lay person not engaged in the business of chemistry or food science technology can easily use the device.

DESCRIPTION OF RELATED ART

There are currently at least two verified, laboratory-based methods for detecting and measuring acrylamide content in food substances: 1) liquid chromatography tandem (or two-stage) mass spectrometry (LC-MS/MS), and 2) gas chromatography-mass spectrometry (GC-MS). No prior art exists describing a quick, reliable, non-laboratory test kit that can be used to easily detect and measure acrylamide concentrations in food substances.

The following patents and patent applications discuss detection of foreign substances (chemical, biological, and otherwise) in food, many of which use the device and method as a kit; however, no prior art exists that references specifically the detection and determination of acrylamide in food substances using a quick and reliable detection means for the average consumer.

U.S. Pat. No. 3,995,164 describes a method and device for the detection of foreign material in food substances. The invention relies on X-ray technology to detect foreign substances in food. This invention is used in a commercial setting.

U.S. Pat. No. 6,544,729 describes a bioluminescent biosensor device. It is a kit that is used for detection of bacteria based on recognition and infection of one or more selected strains of bacteria with bacteriophage genetically modified to cause production of an inducer molecule in the bacterium following phage infection. The inducer molecule is released from the infected bacterium and is detected by genetically modified bacterial bioreporter cells designed to emit bioluminescence upon stimulation by the inducer. Autoamplification of the bioluminescent signal permits detection of low levels of bacteria without sample enrichment. Also disclosed are methods of detection for select bacteria and kits for detection of select bacteria based on the described technology.

U.S. Pat. No. 6,004,747 describes salmonella identification by the polymerase chain reaction. The invention provides nucleic acid molecules for the detection and identification of *Salmonella* species, methods for detecting one or more *Salmonella* serotypes using the nucleic acid molecules of the invention as probes or primers in DNA-based detection systems and kits for carrying out the invention.

WO03032291A2 describes a method and device for performing automated, industrial analysis and/or classification of food substance. The food substances are conveyed by at least one conveying device to a measuring section in which the food substances, after at least partially eliminating gases and/or liquids that are foreign to the food substances, are measured with regard to physical, biological and/or chemical properties. This enables a highly precise and rapid detection of, for example, contaminated food substances and a subsequent sorting out thereof. Likewise, it is possible to precisely sort food substances according to their constituents.

WO02084302A3 describes an interactive system for analyzing biological samples and processing related information and the use thereof. The patent is for an interactive system for chemical and biological testing with the instant data processing and information analysis capability. The system utilizes a specially designed bio-disc and an optical reader attached to a computer to deliver a wide range of tests, such as clinical laboratory diagnostic tests, biological warfare agent detection, forensic DNA tests, and food and water contamination tests, to a remote location.

WO0171316A3 describes one-dimensional arrays on optical fibers using linear arrays of chemosensors or chemical compounds that are supported by an optical fiber that allows one to rapidly assay the entire array using changes in optical properties such as fluorescence. The location of the agent along the fiber determines the identity of the agent in these linear arrays. Combinatorial libraries may be constructed on the fiber as well as assayed on the optical fiber. A system and method of analyzing the entire array of agents on an optical fiber using a light source, an optical fiber, and a detector are also described. The time delay between the excitation and detection determines the location being assayed along the fiber and therefore the identity of the agent being assayed. The invention may find uses in the medical, pharmaceutical, environmental, defense, and food industries.

The following patent application discusses a method for the detection and measurement of ammonia.

US Patent No. 2003/0003589 describes a device and method for detecting and measuring volatile acidic or basic components including ammonia, ammonium, or volatile amines (compound) in a gas or liquid state fluid. The invention provides a PTFE-carrier solid phase indicator film having an ammonia-sensitive indicator dye embedded therein, such that the dye moiety changes color or spectral properties upon exposure to the compound to be detected.

The following patent discusses the use of nitrilase as an enzyme and conversion mechanism and is incorporated herein by reference.

U.S. Pat. No. 5,998,180 describes the following; nitrilase enzymes are provided which have Km at pH 7.0 for acrylonitrile of 500 μM or below. The enzymes also have Ki at pH 7.0 for ammonium acrylate of at least 100 mM. In particular, the nitrilases have a value of the ratio of the said Ki to the said Km of at least 200. Particularly preferred nitrilases are obtainable from the microorganisms *Rhodococcus rhodochrous* NCIMB 40757 or NCIMB 40833. These nitrilases can be used in processes of converting acrylonitrile to ammonium acrylate in aqueous or vapor form and for detecting low levels of nitrile in aqueous or vapor form. In the present invention, the reverse reaction is of use where $NH_3OH^-Na^+$ and nitrilase in solution with the acrylamide would form acrylonitrile, which is then easily detectable. The key measurement parameter is the consumption of ammonium salt which is measured as ammonia by the ion selective electrode(s).

The following science journal articles describe methods using enzymes to breakdown substances, such as degrading amides, or in the case of this invention, degrading acrylamide, via an enzymatic conversion.

An article of significance is *Metabolism of acetonitrile and propionitrile by Nocardia rhodochrous LL100-21*, by M J, Antoine A D, Appl Environ Microbiol. 1976 June; 31(6):900-6. Six nitrile compounds and two amide derivatives were degraded by *Nocardia rhodochrous* LL100-21. Acetonitrile, hydroacrylonitrile, and propionitrile were the best sources of carbon and nitrogen for growth, whereas butenenitrile, succinonitrile, and acetamide supported less growth. Acrylonitrile and acrylamide supported growth but only as a source of nitrogen. Gas chromatography of the culture medium revealed a decrease in acetonitrile with the sequential formation of acetamide and acetic acid. Ammonia was also detected by calorimetric procedures. The enzyme system responsible for the hydrolysis of acetonitrile was shown to be intracellular and inducible. The breakdown of acetonitrile by a crude bacterial extract was a two-step enzymatic hydrolysis with acetamide as the intermediate product and acetic acid and ammonia as the final products. Product formation was stoichiometric with substrate disappearance. When propionitrile was the growth substrate, there was complete conversion of the nitrile to propionic acid and ammonia as the major products. The enzymatic breakdown of the propionitrile, although slower than acetonitrile, yielded the corresponding carboxylic acid and ammonia. Propionamide was produced in very small amounts as an intermediate product.

In this case, detection of the nitrogen caused by degrading the acrylamide using *Nocardia rhodochrous* LL 100-21 can be detected colorimetrically in the form of ammonia or as the nitrogen itself in gaseous form. Ammonia specific membranes in the form of electrodes are commercially available to make these same measurements. Again, in the present invention, the reverse reaction is of use where $NH_3OH^-Na^+$ and nitrilase in solution with the acrylamide would form acrylonitrile, which is then easily detectable. The key measurement parameter is the consumption of ammonium salt which is measured as ammonia by the ion selective electrode(s).

Another article of significance is *Differential regulation of amidase-and formamidase-mediated ammonia production by the Helicobacter pylori fur repressor* by van Vliet A H, Stoof J, Poppelaars S W, Bereswill S, Homuth G, Kist M, Kuipers E J, Kusters J G., Department of Gastroenterology and Hepatology, Erasmus MC University Medical Center Rotterdam, 3015 GD Rotterdam, The Netherlands. a.h.m.vanvliet@eramusmc.nl, J Biol Chem. 2003 Mar. 14; 278(11):9052-7. Epub 2002 Dec. 23, The production of high levels of ammonia allows the human gastric pathogen *Helicobacter pylori* to survive the acidic conditions in the human stomach. *H. pylori* produces ammonia through urease-mediated degradation of urea, but it is also able to convert a range of amide substrates into ammonia via its AmiE amidase and AmiF formamidase enzymes. Here data are provided that demonstrate that the iron-responsive regulatory protein Fur directly and indirectly regulates the activity of the two *H. pylori* amidases. In contrast to other amidase-positive bacteria, amidase and formamidase enzyme activities were not induced by medium supplementation with their respective substrates, acrylamide and formamide. AmiE protein expression and amidase enzyme activity were iron-repressed in *H. pylori* 26695 but constitutive in the isogenic fur mutant. This regulation was mediated at the transcriptional level via the binding of Fur to the amiE promoter region. In contrast, formamidase enzyme activity was not iron-repressed but was significantly higher in the fur mutant. This effect was not mediated at the transcriptional level, and Fur did not bind to the amiF promoter region. These roles of Fur in regulation of the *H. pylori* amidases suggest that the *H. pylori* Fur regulator may have acquired extra functions to compensate for the absence of other regulatory systems.

Another article of significance is *The AmiE aliphatic amidase and AmiF formamidase of Helicobacter pylori: natural evolution of two enzyme paralogues* by S, Labigne A, De Reuse H., Mol Microbiol. 2001 May; 40(3):596-609, Unite de Pathogenie Bacterienne des Muqueuses, Institut Pasteur, 28 rue du Docteur Roux, 75724 Paris Cedex 15, France.sskoulou@jhunix.hcf.jhu.edu. Aliphatic amidases (EC 3.5.1.4) are enzymes catalyzing the hydrolysis of short-chain amides to produce ammonia and the corresponding organic acid. Such an amidase, AmiE, has been detected previously in *Helicobacter pylori*. Analysis of the complete *H. pylori* genome sequence revealed the existence of a duplicated amidase gene that we named amiF. The corresponding AmiF protein is 34% identical to its AmiE paralogue. Because gene duplication is widely considered to be a fundamental process in the acquisition of novel enzymatic functions, we decided to study and compare the functions of the paralogous amidases of *H. pylori*. AmiE and AmiF proteins were overproduced in *Escherichia coli* and purified by a two-step chromatographic procedure. The two *H. pylori* amidases could be distinguished by different biochemical characteristics such as optimum pH or temperature. AmiE hydrolysed propionamide, acetamide and acrylamide and had no activity with formamide. AmiF presented an unexpected substrate specificity: it only hydrolyzed formamide. AmiF is thus the first formamidase (EC 3.5.1.49) related to aliphatic amidases to be described. Cys-165 in AmiE and Cys-166 in AmiF were identified as residues essential for catalysis of the corresponding enzymes. *H. pylori* strains carrying single and double mutations of amiE and amiF were constructed. The substrate specificities of these enzymes were confirmed in *H. pylori*. Production of AmiE and AmiF proteins is dependent on the activity of other enzymes involved in the nitrogen metabolism of *H. pylori* (urease and arginase respectively). Our results strongly suggest that (i) the *H. pylori* paralogous amidases have evolved to achieve enzymatic specialization after ancestral gene duplication; and (ii) the production of these enzymes is regulated to maintain intracellular nitrogen balance in *H. pylori*.

In this instance, one would use AmiE to hydrolyze acrylamide and detect the hydrolyzed version of the concentration of acrylamide in solution by a change in pH, temperature, or calorimetrically and perhaps by IR once the chemical functionality of the hydrolyzed version of the acrylamide is fully characterized.

Another article of significance is *Nitrilase of Rhodococcus rhodochrous J1: Conversion into the active form by subunit association*, by Toru Nagasawa, Marco Wieser, Tetsuji Nakamura, Hitomi Iwahara, Toyokazu Yoshida and Kunihiko Gekko *European Journal of Biochemistry*, 267, 138-144 (2000). Nitrilase-containing resting cells of *Rhodococcus rhodochrous* J1 converted acrylonitrile and benzonitrile to the corresponding acids, but the purified nitrilase hydrolyzed only benzonitrile, and not acrylonitrile. The activity of the purified enzyme towards acrylonitrile was recovered by preincubation with 10 mM benzonitrile, but not by preincubation with aliphatic nitrites such as acrylonitrile. It was shown by light-scattering experiments, that preincubation with benzonitrile led to the assembly of the inactive, purified and homodimeric 80-kDa enzyme to its active 410-kDa aggregate, which was proposed to be a decamer. Furthermore, the association concomitant with the activation was reached after dialysis of the enzyme against various salts and organic solvents, with the highest recovery reached at 10% saturated ammonium sulfate and 50% (v/v) glycerol, and by preincubation at increased temperatures or enzyme concentrations.

The following articles discuss known prior art used for analytical detection and measurement of acrylamide concentrations in food substances. They focus on the two main laboratory-based methods of acrylamide detection: 1) liquid chromatography tandem (or two-stage) mass spectrometry (LC-MS/MS), and 2) gas chromatography-mass spectrometry (GC-MS).

A recent article of significance includes, "*Analysis of acrylamide in cooked foods by liquid chromatography tandem mass spectrometry*," Johan Rosén and Karl-Erik Hellenäs. Analyst. 2002 July; 127(7):880-2, where a method using liquid chromatography tandem mass spectrometry (LC-MS-MS) with electrospray for the analysis of acrylamide in foods is reported. The method comprises the addition of deuterium-labeled acrylamide-$d_3$, extraction with water, mixed mode solid phase extraction, ultrafiltration and a graphitized carbon column for chromatography. The transitions m/z 72>55, 72>54, 72>44, 72>27, 72>72 and 75>58 were recorded in multiple reaction monitoring mode for identification and determination. In-house validation data for products from potatoes and cereals (30 to 10 000 µg kg$^{-1}$) are presented (accuracy 91 to 102%, relative standard deviation 3 to 21%). Interlaboratory validation data (comparison with gas chromatography mass spectrometry, 25 to 2000 µg kg$^{-1}$) showed excellent results ($r^2$=0.998).

An additional article of significance includes, "*Analysis of acrylamide by LC-MS/MS and GC-MS in processed Japanese foods*," H Ono, Y Chuda, M Ohnishi-Kameyama, H Yada, M Ishizaka, H Kobayashi, M Yoshida, Food Additives & Contaminants, Volume 20, Number 3/2003, 215-220 that indicates that acrylamide concentrations in processed foods (63 samples covering 31 product types) from Japan were analyzed by LC-MS/MS and GC-MS methods. The limit of detection and limit of quantification of acrylamide were 0.2 ng ml$^{-1}$ (6 fmol) and 0.8 ng ml$^{-1}$ (22 fmol), respectively, by LC-MS/MS, and those of 2,3-dibromopropionamide derived from acrylamide were 12 ng ml$^{-1}$ (52 fmol) and 40 ng ml$^{-1}$ (170 fmol), respectively, by GC-MS. Repeatability given as RSD was <5 and <15% for the LC-MS/MS and GC-MS methods, respectively. High correlation ($r^2$ m 0.946) was observed between values obtained by the two methods. Most potato crisps and whole potato-based fried snacks showed acrylamide concentrations>1000 µmg kg$^{-1}$. The concentrations in non-whole potato-based snacks, rice crackers processed by grilling or frying, and candied sweet potatoes were lower compared with those in the potato crisps and the whole potato-based fried snacks. One of the whole potato-based fried snacks, however, showed low acrylamide concentration (<50 µg kg$^{-1}$) suggesting the formation of acrylamide is strongly influenced by processing conditions. Acrylamide concentrations in instant precooked noodles and won-tons were <100 µg kg$^{-1}$ with only one exception. Roasted barley grains for 'Mugi-cha' tea contained 200-600 µg kg$^{-1}$ acrylamide.

An additional article of significance includes, "*Verification of the findings of acrylamide in heated foods*," J S Ahn, L Castle, D B Clarke, A S Lloyd, M R Philo, D R Speck, Food Additives & Contaminants, Volume 19, Number 12, Dec. 1, 2002. Reported here is the first confirmation of the recent Swedish findings of acrylamide in heated foods. The verification exercise used an LC-MS/MS method developed for the purpose as well as an established GCMS method for acrylamide analysis. LC-MS/MS was suitable for the direct determination of acrylamide in aqueous extracts of foods by isotope dilution mass spectrometry (IDMS) using triply deuterated acrylamide. Some food matrices were not suited to the new method and mixed-mode solid-phase extraction (SPE) was used to clean these extracts. The foods tested included UK versions of some of the key food groups analyzed in Sweden. Also tested were some foods heated under home-cooking conditions. There was good agreement between the LC-MS/MS results and the GC-MS results and the concentrations of acrylamide found here were similar to those reported for the corresponding foods analyzed in the Swedish study. The analyses confirmed that acrylamide is absent from the raw or boiled foods but present at significant concentrations in fried, grilled, baked and toasted foods. The highest result was 12000 µg kg$^{-1}$ acrylamide in overcooked oil-fried chips.

SUMMARY OF THE INVENTION

The present invention is a device in the preferred embodiment of a kit and associated analytical method including a biochip that is used for the sensitive detection and accurate, rapid determination of acrylamide concentrations in food substances. The device and method is one in which the user can quickly and easily ascertain the amount of acrylamide in food substances while in a home or non-laboratory environment. In addition, food processing conditions may be changed to eliminate or greatly reduce the formation of acrylamides by various means.

This detection device and method may be comprised of the sample collection area on which the sample of food, after being mixed in a solution, is placed, for example, on the substrate of a biochip that includes an enzyme, such as nitrilase from *Nocardia rhodochrous* LL 100-21 or AmiE aliphatic amidase, if necessary along with a co-enzyme or form of energy or catalyst that facilitates the conversion of acrylamide to acrylonitrile or the conversion of acrylamide to ammonia or a nitrogen containing compound or the like. The kit-like device would utilize an ammonia-sensitive or acrylonitrile-sensitive film strip, a colorimetric display showing the amount of ammonia or acrylonitrile detected in the sample, a chromophore such as bromophenol blue, bromocresol green, or chlorophenol red which shows detection by color change, and a colorimetric scale to provide the kit user with the concentration of acrylonitrile or ammonia present, which is scaled to be representative of the concentration of acrylamide in the food substance (using the acrylonitrile or ammonia calibration curve as a control). If acrylamide is detected in the sample food substances, the resultant concentration, as determined on the colorimetric scale, provides the consumer of the food substances opportunity to reject or discard the substance prior to consumption.

A further embodiment of the present invention relates to a mechanical or electrical detection kit, similar to the colorimetric kit above, however which utilizes the same pH scaled principals in obtaining a numeric or digital readout of the concentration of acrylamide detected within a sample of food. Mechanical or electrical scales which are currently used to measure pH could be modified by one skilled in the art to create the inventive embodiment of the present invention in determining acrylamide concentrations in samples of food, and reducing the health risks associated with the effects of such a potent toxin.

Furthermore, any of the detection devices of the present invention may be utilized above to make a determination of at least trace amounts of acrylamides, whereupon such samples taken and results obtained may be sent to a laboratory for further testing, utilizing gas chromatography or mass spectrometry or a combination thereof to determine exact amounts of acrylamide within the sample.

Another variation of the detection device above may utilize infrared (IR) spectrometry to measure a liquid sample and determine the amount of acrylonitrile or ammonia within the sample. For example, with acrylonitrile, the detection device may utilize an IR chemical sensor that identifies the very sharp absorption peak of the carbon-nitrogen C≡N triple bond in acrylonitrile. Because the C≡N triple bond is absorbed strongly in the IR spectra at 2250 cm$^{-1}$ wavelength, a hand-held or laboratory-based infrared sensor can be used to measure the IR adsorption. This provides a method to measure acrylonitrile precisely and accurately. The IR measurement component may be part of the test kit device or alternatively may be part of a test kit that is sent in to a laboratory for further analysis at that laboratory site.

Another variation of the detection device above may utilize a LUMI-CELL™ Assay that applies the knowledge of the toxic mechanisms of polychlorinated diaromatic hydrocarbons (PCDH). PCDH include dioxins and other toxic compounds that have been known to accumulate in animals and cause species and tissue-specific toxic effects. Birth defects, immune system disorders, tumor production, etc., have all been observed as a result of high level exposure to PCDH. It is anticipated that digestion of foods that contain high levels of acrylamides will cause similar toxic effects. The amount of PCDH in the sample is related to how much light is produced by the activated cells used by this technology. It is anticipated that a similar mechanism will occur with acrylamides being substituted for PCDH and that binding to specific DNA sequences or proteins will occur therefore allowing the use of the same technique and technology to measure acrylamide concentrations to less than the parts per trillion level. This technique has been pioneered and championed by Drs. George C. Clark and Michael S. Denison and is fully described in U.S. Pat. No. 5,854,010 herein incorporated by reference.

Another embodiment of the present invention exists in making a test method available that could be used outside of the laboratory (as well as within a laboratory—as is the case for the other methods listed above), using that a reactive species within the acrylamide that is made available to react with an amino acid in a protein. If this occurs within an animal (such as a mouse) that carries the specific protein, the body that carries the protein will "see" these reactive products as "foreign proteins" and production of monoclonal antibodies will occur. This decouples the test methodology from the cellular level as described in previous methods above. It is possible to then couple the antibodies with a color dye to indicate the concentration of antibodies that bind to the protein, while rinsing away those that do not bind. This method would also produce a very highly sensitive test method and one that could be combined with a biochip for other than laboratory use (home or office use).

A further embodiment of the present invention is to eliminate or greatly reduce acrylamides in (primarily processed) food or foodstuffs by lowering process temperatures, removing or reducing the concentration of reducing sugars, and/or adding acidic or basic or other food additive components. The later method (addition of food additives) would shift the acrylamide formation reaction(s) toward lower undesirable (acrylamide) product yields or completely change the reaction and thus eliminate or greatly reduce the formation of acrylamide.

DETAILED DESCRIPTION

Figure 1:
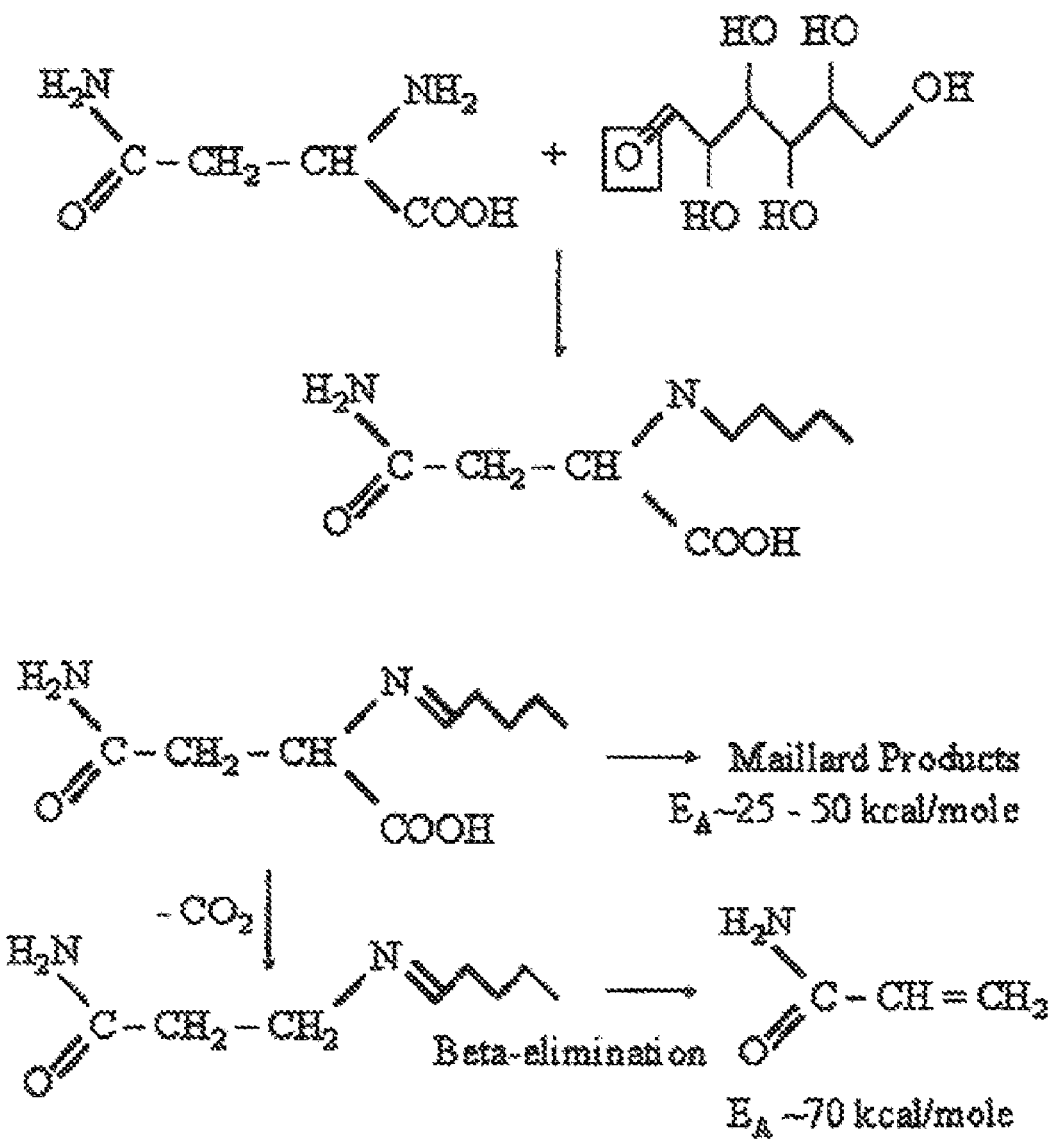
FIG. 1 shows a possible mechanism for the formation of acrylamide from asparagine. The chemical structures shown illustrate how the Maillard reaction can produce acrylamides in food when asparagine, a sugar, and/or a carbohydrate are present.

The description below is an example of how the concentration of acrylamide in a food substance could be measured colorimetrically using an aliphatic amidase, AmiE that can convert the acrylamide into ammonia or other nitrogen containing compounds. Similar techniques are also anticipated by this invention using other enzymes or techniques that may convert or degrade the acrylamide present in food into other chemical fragments that are easily and readily detectable by one of several techniques including colorimetric, pH change, temperature change, etc. Techniques where acrylamides may not have to be converted into other chemical fragments to be detected are also anticipated by this invention.

The gene for the aliphatic amidase, AmiE, from *H. pylori* is amplified by PCR and cloned into pUC19. Genes from *P. aeruginosa*, *Rhodococcus* sp. R312 or *B. stearothermophilus* encoding other short-chain amidases would work equally as well. The resultant plasmid is used to transform *E. coli*. The cells can be grown in Luria broth and harvested by centrifugation. Cells are disrupted by grinding in a Dynomill and the resultant cell extract is clarified by centrifugation. The amidase is purified from the crude cell extract by anion exchange chromatography where the amidase is found in the unbound fraction. The amidase containing solution is concentrated by ultrafiltration on a 10,000 MW cutoff membrane and further purified by size exclusion chromatography. The purified enzyme fractions are concentrated by ultrafiltration and diafiltered against 20 mM sodium phosphate, pH 7.0. The purified enzyme solution is dried onto a PTFE-carrier solid phase indicator film having an ammonia-sensitive indicator dye embedded therein, such that the dye moiety changes color upon exposure to the compound to be detected.

The sample of food to be analyzed is suspended in a minimal amount of water and macerated. A drop of the water/macerated food substance is placed onto the PTFE film-amidase complex and allowed to react for a pre-determined time interval. As a control a separate drop of water is added to the film in a second location. If a color change is observed for the macerated food substances as compared to the water control, acrylamides are present. The intensity of the color change can be calibrated so that the concentration of the acrylamide in the macerated food substance can be determined.

Another technique anticipated by this invention uses nitrilase to convert or degrade any acrylamide concentration present in the sample food substance into acrylonitrile, an easily detectable chemical fragment of acrylamide. This technique relies on the reaction where $NH_3OH^-Na^+$ and nitrilase, such as from *Rhodococcus rhodochrous* NCIMB 40757 or NCIMB 40833, in solution with the acrylamide would form acrylonitrile.

According to this method of the invention, acrylamide is detected in a sample of food by:

(a) collecting a food sample, placing the food sample in a solution for dissolving, and subsequently placing it onto a substrate of a test device where the substrate is comprised of nitrilase and a co-enzyme and/or energy source and/or catalyst facilitating the conversion of acrylamide to acrylonitrile;

(b) allowing the acrylamide conversion to acrylonitrile on the nitrilase substrate;

(c) measuring the consumption of ammonium salt which is measured as ammonia by an ion selective electrode; and (d) using a scale converting the concentration of ammonia to the concentration of acrylamide, thus giving the concentration of acrylamide that was present in the food sample.

Once nitrilase has been used to facilitate the conversion of acrylamide to acrylonitrile, the detection of acrylonitrile present may optionally be determined by utilizing an infrared (IR) sensor measuring a sample and determining the concentration of acrylonitrile within the sample by an absorption peak of the carbon-nitrogen (C≡N) triple bond in acrylonitrile in an IR spectra at 2250 $cm^{-1}$ wavelength.

The nitrilase used to facilitate the conversion of acrylamide to acrylonitrile may be present in a biochip in an aqueous environment, for instance a liquid aqueous environment or a water-containing gel.

According to U.S. Pat. No. 5,998,180, which is incorporated by reference herein, the following is noted. The change may be for instance a change in conductivity in the aqueous environment. Nitriles are non-ionic species and therefore cannot be detected using conductivity measurement. If they are converted to ionic species, that is ammonium salts, the resulting change in conductivity can be measured. Alternatively a change in ammonium ion concentration can be detected or a system of linked enzymes can be used to detect a change.

The nitrilases of the present invention are particularly useful in nitrilase biosensors due to, in particular, capacity to show a substantially linear response to extremely low concentrations of nitrile.

Generally enzyme is used in the purified extracted form. However, enzyme may be used in whole cell form or as a bacterial cell fraction.

A process where the nitrile-containing vapor is contacted with the nitrilase and is converted to its corresponding ammonium salt exists so that nitrile is reduced to below 5 $mg/m^3$, or even below 2 $mg/m^3$ (2 ppm). Contact is normally made in an aqueous environment, for instance a liquid aqueous environment or a water-containing gel, or simply with damp enzyme.

This method is particularly useful for detecting very low levels of nitrile on-line which are not detectable by other methods. Using this method, the nitrilase may be any nitrilase according to the invention but it is preferred that the nitrilase has a Km for the nitrile being detected of 500 µM or below, preferably 100 µM or below, more preferably 50 µM or below. Most preferably the nitrilase is one obtainable by culturing *R. rhodochrous* NCIMB 40757 or the newly deposited strain NCIMB 40833.

Another variation of the detection device above may utilize a LUMI-CELL™ Assay that applies the knowledge of the toxic mechanisms of polychlorinated diaromatic hydrocarbons (PCDH). PCDH include dioxins and other toxic compounds that have been known to accumulate in animals and cause species and tissue-specific toxic effects. Birth defects, immune system disorders, tumor production, etc., have all been observed as a result of high level exposure to PCDH. It is anticipated that digestion of foods that contain high levels of acrylamides will cause similar toxic effects.

The mechanism of action for these compounds depends on their ability to bind to an intracellular receptor known as the aromatic hydrocarbon Receptor (AhR). The PCDH-Ah Receptor complex travels to the nucleus of the cell and binds to specific sequences in DNA known as dioxin responsive elements (DRE). Binding of the PCDH-Ah receptor complex to a DRE causes expression of the associated gene to be altered. It is this alteration in gene expression that causes observed toxic effects. Using recombinant technology, the gene for the firefly luciferase has been replaced under control of the Ah Receptor and inserted into a mouse cell line. Using this cell line, the presence of PCDH in a sample can be identified because PCDH will bind to the Ah Receptor, which will then bind to the DRE in the nucleus and cause expression of the firefly luciferase or green fluorescence protein or red fluorescence protein using a fluorimeter to indicate activity which is proportional to concentration. The amount of PCDH in the sample is related to how much light is produced by the activated cells. It is anticipated that a similar mechanism will occur with acrylamides being substituted for PCDH and that binding to specific DNA sequences similar to DRE's will occur therefore allowing the use of the same technique and technology to measure acrylamide concentrations to less than the parts per trillion level. This technique has pioneered and championed by Drs. George C. Clark and Michael S. Denison and is fully described in U.S. Pat. No. 5,854,010 herein incorporated by reference.

Another possibility that exists in preparing a test method that could be used outside of the laboratory (as well as within a laboratory—as is the case for the other methods listed above), is that a reactive species within the acrylamide is made available to react with an amino acid in a protein. If this occurs within an animal (such as a mouse) that carries the protein, the body that carries the protein will "see" these reactive products as "foreign proteins" and production of monoclonal antibodies will occur. This decouples the test methodology from the cellular level as described in previous methods above. It is possible to then couple the antibodies with a color dye to indicate the concentration of antibodies that bind to the protein, while rinsing away those that do not bind. This method would also produce a highly sensitive test method and one that could be combined with a biochip for other than laboratory use (home or office use). One skilled in the art will immediately recognize the simplicity and ease with which this methodology can be employed.

What is claimed is:

1. A method for determining a specific concentration of acrylamide in a sample of any food or food substance comprising the following steps:

collecting a sample of said food substance and mixing with a solution for dissolving said food substance and; subsequently placing said solution onto a substrate of a testing device; said substrate comprising an enzyme that, along with a co-enzyme and/or catalyst, causes converting of acrylamide to acrylonitrile; quantifying the concentration of acrylonitrile within said sample by an absorption peak of the carbon-nitrogen (C≡N) triple bond in acrylonitrile in an IR spectra at 2250 $cm^{-1}$ wavelength with an infrared (IR) sensor; and displaying said concentration of acrylonitrile detected, and providing a scale that is representative of said concentration of said acrylamide in said food substance.

2. The method for determining a specific concentration of acrylamide in a sample of any food or food substance as in claim 1, wherein at least a portion of said testing device is located on a biochip.

* * * * *